United States Patent [19]

Niznick

[11] Patent Number: 5,281,140
[45] Date of Patent: Jan. 25, 1994

[54] MULTI-PART, MULTI-POSITIONABLE ABUTMENT FOR USE WITH DENTAL IMPLANTS

[75] Inventor: Gerald A. Niznick, Encino, Calif.

[73] Assignee: Core-Vent Corporation, Las Vegas, Nev.

[21] Appl. No.: 855,452

[22] Filed: Mar. 19, 1992

Related U.S. Application Data

[63] Continuation of Ser. No. 636,796, Jan. 2, 1991, abandoned.

[51] Int. Cl.$^5$ .................. A61C 8/00; A61C 13/12; A61C 13/225
[52] U.S. Cl. ................................ 433/172; 433/173
[58] Field of Search ............... 433/173, 174, 175, 176, 433/220, 221, 172

[56] References Cited

U.S. PATENT DOCUMENTS

| | | | |
|---|---|---|---|
| 4,722,688 | 2/1988 | Lonca | 433/173 |
| 4,832,601 | 5/1989 | Linden | 433/173 |
| 4,850,870 | 7/1989 | Lazzara et al. | 433/173 |
| 4,854,872 | 8/1989 | Detsch | 433/173 |
| 4,904,187 | 2/1990 | Zingheim | 433/173 |
| 4,988,292 | 1/1991 | Rosen | 433/173 |
| 5,030,095 | 7/1991 | Niznick | 433/173 |
| 5,106,300 | 4/1992 | Voitik | 433/173 |
| 5,135,395 | 8/1992 | Marlin | 433/173 X |
| 5,152,687 | 10/1992 | Amino | 433/173 |

FOREIGN PATENT DOCUMENTS

| | | | |
|---|---|---|---|
| 0323421 | 7/1989 | European Pat. Off. | 433/173 |
| 8803391 | 5/1988 | World Int. Prop. O. | 433/174 |

Primary Examiner—Gene Mancene
Assistant Examiner—Nicholas D. Lucchesi

[57] ABSTRACT

A multi-part abutment adapted for use with dental implants such as cylindrical-shaped endosseous dental implants having an internal opening or passage with an internal, non-circular shape at the top includes part one that sealingly engages the opening or passage in the top of the implant at the bottom end of part one, and engages another abutment part, part two, at the top end of part one through a multi-sided projection. Part two has at its bottom end a multi-sided cavity that interdigitates with the projection from part one so that part two can be seated in a plurality of positions atop part one. At the top end of part two is a prosthesis-engaging or prosthesis-forming projection which can be at an angle to the longitudinal axis of the implant, or lie on the longitudinal axis of the implant. Internal passages inside the two parts are colinear when their parts are joined to one another in their intended configuration, permitting the use of a single fastener to join the two abutment parts to one another and to the opening or passage in the dental implant.

22 Claims, 3 Drawing Sheets

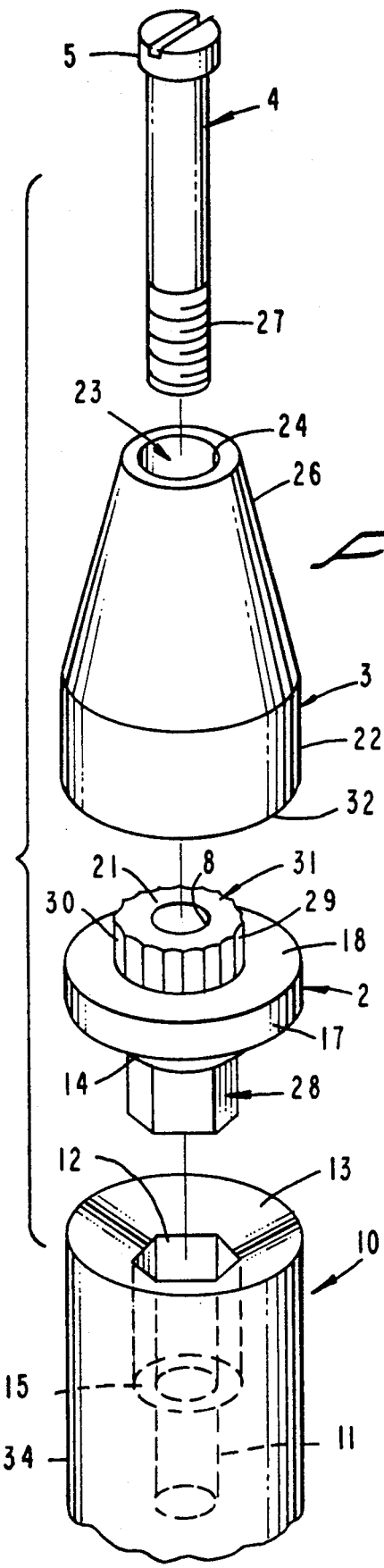
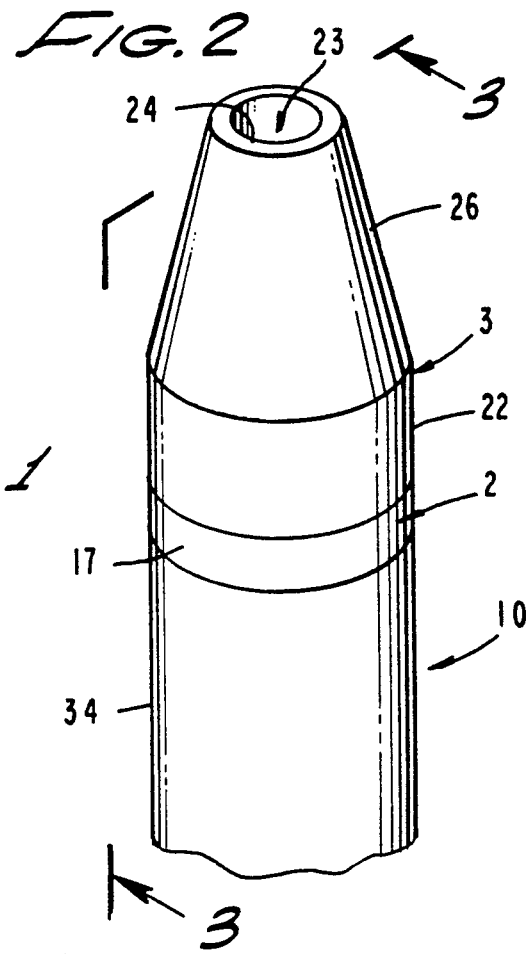
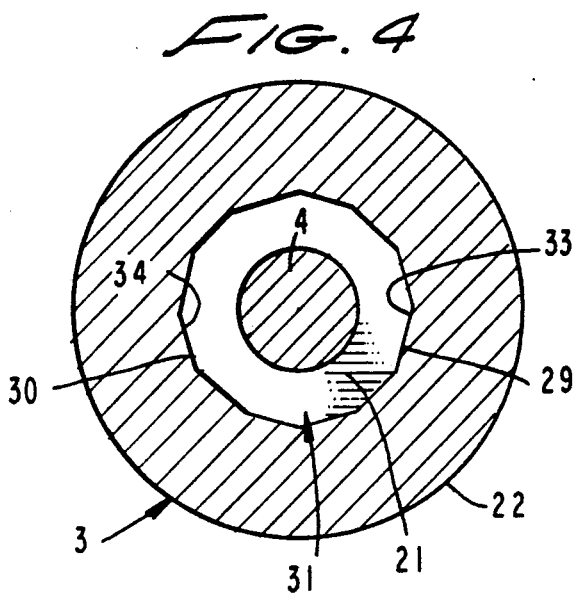

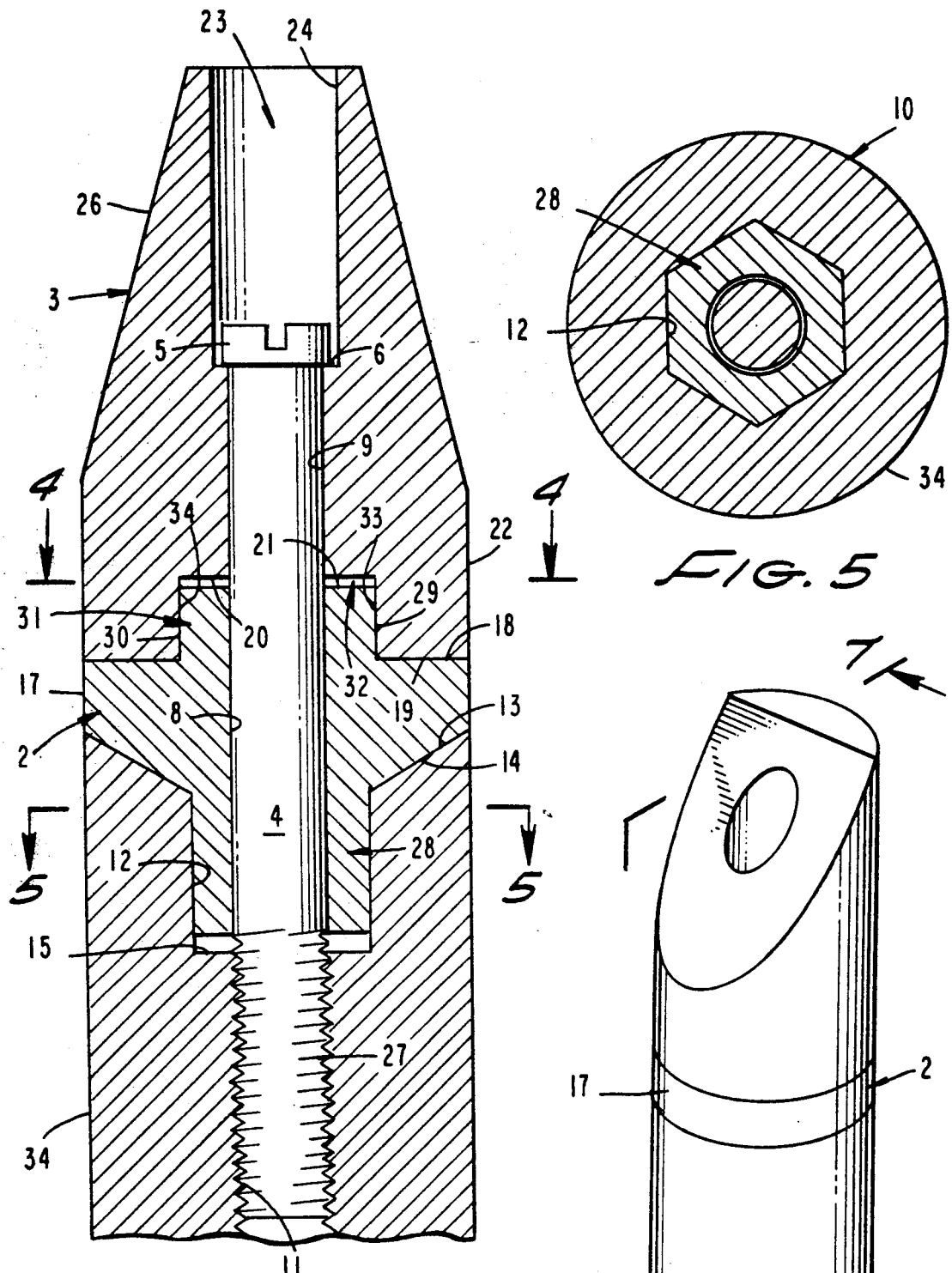
FIG. 3
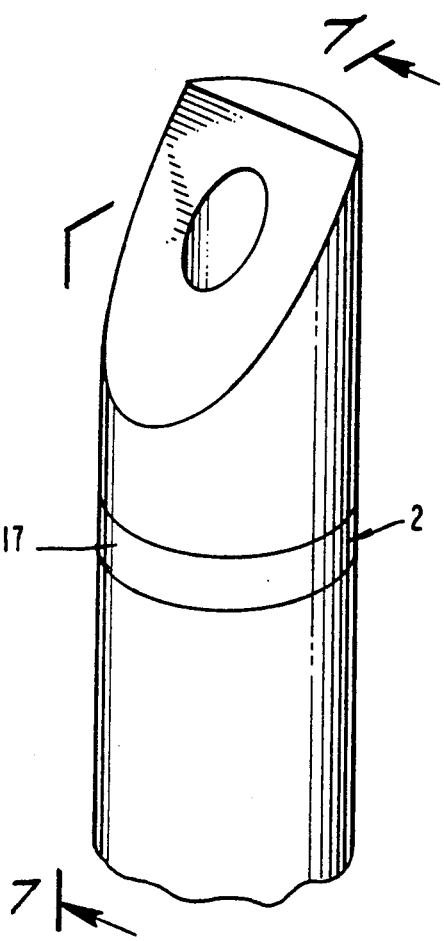
FIG. 5
FIG. 6

MULTI-PART, MULTI-POSITIONABLE ABUTMENT FOR USE WITH DENTAL IMPLANTS

This application is a continuation of application Ser. No. 07/636,796 filed Jan. 2, 1992 for "MULTI-PART, MULTI-POSITIONABLE ABUTMENT FOR USE WITH DENTAL IMPLANTS" by GERALD A. NIZNICK now abandoned.

This invention relates to an abutment adapted for use with dental implants, particularly endosseous dental implants, and, more particularly, cylindrical-shaped endosseous dental implants. This abutment has multiple parts, including an angled head portion that can be placed in any one of a multiplicity of desired positions. In preferred embodiments, these multiple parts are secured to a dental implant by a single fastener that joins the multiple parts of the abutment to one another, and to the implant.

The multi-part abutment of this invention comprises part one having a projection of a shape and size, at the bottom end, that is adapted to fit sealingly, and preferably non-rotatably, into an opening or passage at the top of a dental implant. The bottom end is of a shape and size adapted to sealingly engage the opening or passage in the top of such an implant. In preferred embodiments, this bottom end fits snugly, and non-rotatably, into such a passage or opening so that food, blood, other tissue, and foreign matter are substantially excluded from the opening or passage, and from the interface between part one and the implant opening or passage.

At its top end, part one includes a multi-sided projection, having a size and shape adapted to engage the bottom end of abutment part two of complementary size and shape. In preferred embodiments, the multi-sided projection has, for example, six to twelve faces or sides to permit connection to the second abutment part, which has a complementary cavity or opening with, for example, from six to twelve faces or sides. These complementary configurations permit part two to be placed in any one of these six to twelve positions atop part one.

Parts one and two also include a passage along their longitudinal axes for receiving a fastener. Such a fastener is preferably a shaft that passes through the passage in part two, through a similar, colinear passage in part one, and into the passage or opening at the top of the dental implant. There, the fastener is adapted to engage the passage or opening at the top of the implant. Preferably, a threaded portion at the distal end of the fastener engages complementary threads on the interior wall of the passage or opening in the dental implant.

Part two includes, at its bottom end, a multi-sided cavity of a size, shape and configuration that interdigitates and connects with the projection at the top end of part one. This bottom end of part two has, in preferred embodiments, a multi-sided cavity of six to twelve sides or faces to permit part two to interdigitate in any one of a number of positions atop part one.

Part two has, at its upper end, a prosthesis-engaging or prosthesis-forming portion that can be of any desired size or shape, and formed at any angle with respect to the longitudinal axis of the abutment. In preferred embodiments, this upper end of part two has a frusto-conical shaped portion that lies along the longitudinal axes of the two parts, where it forms an angle with respect to the longitudinal axes of the two parts.

In preferred embodiments, part two, like part one, includes a passage along its longitudinal axis for receiving a fastener. This longitudinal passage is of a size, shape and configuration that is substantially similar to the size, shape and configuration of the longitudinal passage in part one so that a single fastener can pass through both passages, joining abutment parts one and two to one another and to a dental implant. Thus, as in part one, the passage is preferably cylindrical in shape, but also includes a cylindrical-shaped shelf or flange for engaging one end of a single fastener that is adapted to join the two parts to one another, and to a dental implant.

In preferred embodiments, the fastener is a cylindrical-shaped shaft having a threaded portion at its distal end, and having a flange at its upper end that is of a size and shape adapted to engage the shoulder or flange in the interior passage of the other part. Alternatively, the shaft can have, at its distal end, a portion of a size and shape adapted to frictionally engage, or cement into a passage or opening inside the top of the dental implant.

BRIEF DESCRIPTION OF THE DRAWINGS

This invention can better be understood by reference to the drawings, in which:

FIG. 1 is an exploded perspective view of a dental implant and a preferred embodiment of the multi-part abutments comprising this invention;

FIG. 2 is a perspective view of a dental implant to which is attached a preferred embodiment of the multi-part abutments;

FIG. 3 is a side elevational view, in cross-section, taken on lines 3—3 of FIG. 2;

FIG. 4 is a top plan, in cross-section, taken on lines 4—4 of FIG. 3;

FIG. 5 is a top plan, in cross-section, taken on lines 5—5 of FIG. 3;

FIG. 6 is a perspective view of a dental implant to which is attached an alternative form of multi-part abutment;

DESCRIPTION OF THE PREFERRED EMBODIMENTS

Figure 7:
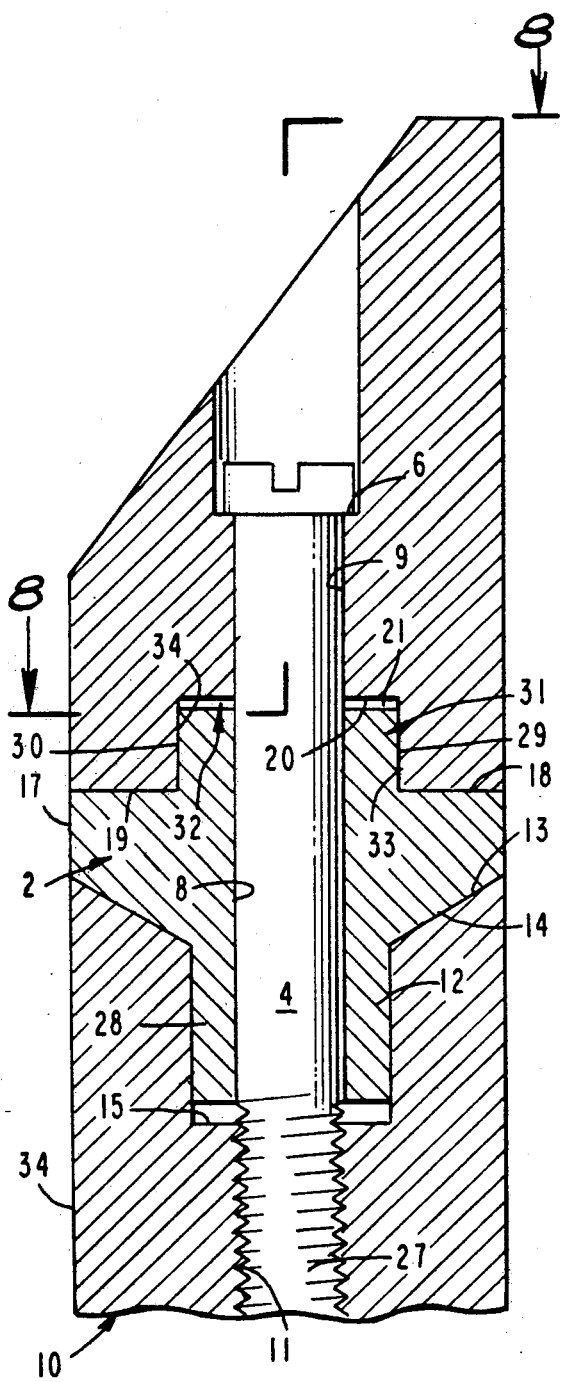
FIG. 7 is a side elevation, in cross-section, taken on lines 7—7 of FIG. 6.

FIGS. 1-5 show an endosseous, cylindrical-shaped dental implant 10. This implant could be, for example, a Core-Vent dental implant, Screw-Vent dental implant, Micro-Vent dental implant, or Bio-Vent dental implant. Implant 10 has, at its upper end, a chamfered shoulder 13. This chamfered shoulder 13 forms an opening leading to hexagonal-shaped opening 12 inside implant 10. Cylindrical-shaped opening 12, includes shelf 15 which extends around the wall of passage 12. Below shelf 15 is internally-threaded, cylindrical-shaped passage 11.

Seated in opening 12 and on shoulder 13 of implant 10 is abutment part one, designated 2. Part 2 includes cylindrically-shaped sidewall 17, which is of substantially the same circumference as sidewall 34 of implant 10. At its lower end, part 2 includes chamfered wall portion 14 which is complementary in size and shape to chamfered surface 13. Part 2 also includes hexagonal-shaped projection 28, which is of a size, shape and configuration to fit sealingly into opening 12. Chamfered surface 14 fits sealingly against chamfered shoulder 13.

At the upper end of part 2 is multi-sided projection 31. Projection 31 has twelve sides or faces, such as sides 29 and 30, which fit sealingly against faces 33 and 34 on top of abutment part two, designated 3. Projection 31 also includes flat upper surfaces 18 and 21. Surfaces 18 and 21 are of a size, shape and configuration adapted to engage and fit sealingly against complementary flat surfaces 19 and 20 on abutment part 3 when parts 2 and 3 are connected to one another.

Part 3, as FIG. 1 shows, has a generally cylindrical shape, with cylindrical wall 22 having substantially the same circumference as cylindrical wall 17 of part 2 and cylindrical wall 34 of implant 10. At the bottom end of part 3 is cavity 32, which includes a plurality of sides or faces such as faces 33 and 34. These faces 33 and 34 are substantially equal in size, shape and configuration to faces 30 and 29 on projection 31 of part 2. Cavity 32 includes flat, substantially circular face 20 of a size and shape adapted to sealingly engage flat, cylindrically-shaped surface 21 at the top of part 2. Part 3 also includes flat, cylindrically-shaped surface 19 which is of a size and shape adapted to sealingly engage flat cylindrically-shaped surface 18 on part 2.

At the upper end of part 3 is conical-shaped prosthesis-forming or prosthesis-engaging portion 26. This portion has a cylindrical-shaped internal passage 23 with smooth, cylindrical-shaped wall 24 terminating in circular-shaped shoulder 6. Internal passage 23 continues below shoulder 6 with internal passage 9 which has a size and shape substantially the same as internal passage 8 in part 2. Passages 8 and 9 lie in end-to-end alignment when parts 2 and 3 are joined together as intended.

Within passage 9 of part 3 and passage 8 of part 2 is fastener 4. Fastener 4 has a cylindrical shaft that extends downwardly from flange 5 at the upper end of fastener 4 to threaded distal end portion 27. Threaded portion 27 screws into and engages interior threads 11 in the passage inside implant 10. The bottom surface of flange 5 is seated upon shoulder 6 inside passage 23 in part 3. Thus, fastener 4 joins part 3 to part 2, and in turn joins parts 2 and 3 to implant 10.

In use, part 2 is seated on shoulder 13 of implant 10, and part 3 is then placed onto part 2 in any desired one of the twelve circumferentially-spaced positions defined by the twelve faces on projection 31.

Figure 8:
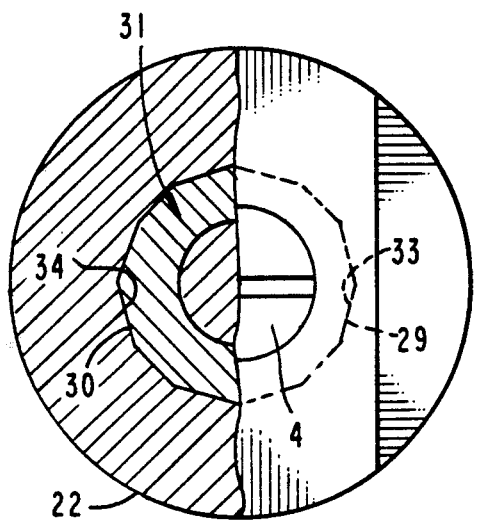
FIG. 8 is a top plan, in cross-section, taken on lines 8—8 of FIG. 7.
Figure 9:
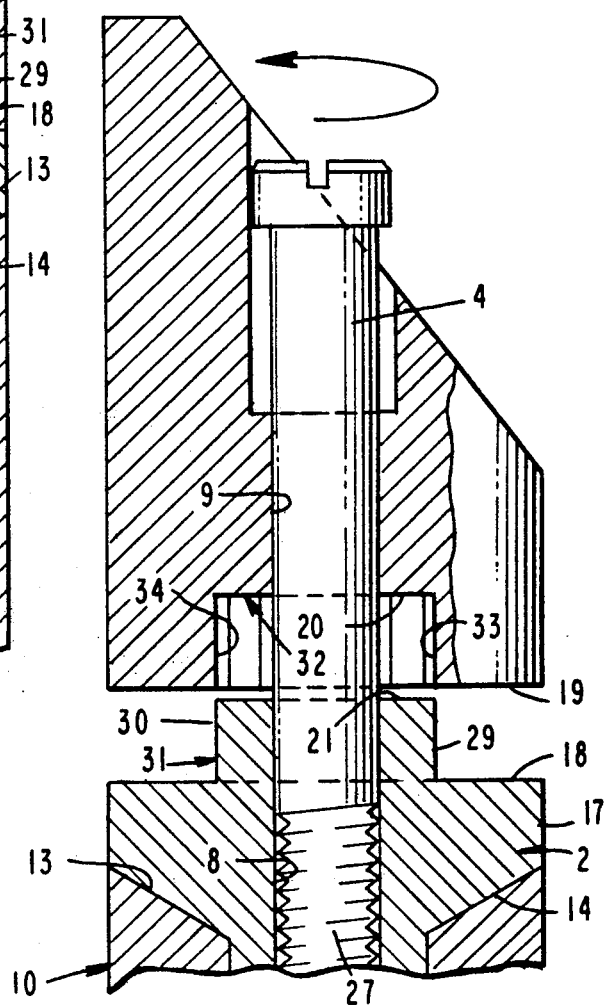
FIG. 9 is a side elevational view, in cross-section, similar to FIG. 7 illustrating the rotational mans of the frusto-conical abutment.

FIGS. 6-9 show the same endosseous, cylindrical-shaped dental implant 10 as FIGS. 1-5, and a two-part abutment substantially the same as the two-part abutment shown in FIG. 1-5. Here, however, part 40 includes slanted upper face 42. Slanted upper face 42 includes cylindrical-shaped internal passage 43 with smooth, cylindrical-shaped inner walls 44 (see FIG. 7) terminating in circular-shaped shoulder 45.

In use, part 2 is seated on shoulder 13 of implant 10, and part 40 is then placed on part 2 in any desired one of the twelve circumferentially-spaced portions defined by the twelve faces on projection 31.

What is claimed is:

1. A two-part abutment for use with a dental implant having an opening or passage with an internal, non-circular shape at its upper end and comprising: part one having a size and shape, at its bottom end, which is unthreaded and which is adapted to fit unthreadedly, non-rotatably and sealingly into said opening or passage, and, at its top end, projection means having a plurality of sides to engage abutment part two in a plurality of peripherally spaced positions; part two having means at its bottom end to sealingly, unthreadedly, non-rotatably engage said projection, said part two having a cavity of a size and shape complementary to said projection, and adapted to sealingly engage said projection in a plurality of spaced positions; said part two including a top end portion adapted to engage or form or a prosthesis; said part one and said part two including substantially colinear, internal passages for receiving a single threaded fastener to join said part one and said part two to one another, and to the interior opening or passage in said dental implant.

2. The abutment of claim 1 wherein said top end portion lies at an angle with respect to the longitudinal axis of said abutment.

3. The abutment of claim 2 further comprising a single fastener of a size, shape and configuration adapted to join said part one and said part two to one another and to the interior opening or passage in said dental implant.

4. The two-part abutment of claim 3 further comprising, at said bottom end of said part one, a plurality of sides, said implant having the same number of sides as said bottom end in said opening or passage.

5. The two-part abutment of claim 2 further comprising, at said bottom end of said part one, a plurality of sides, said implant having the same number of sides as said bottom end in said opening or passage.

6. The abutment of claim 1 further comprising a single fastener of a size, shape and configuration adapted to join said part one and said part two to one another and to the interior opening or passage in said dental implant.

7. The two-part abutment of claim 6 further comprising, at said bottom end of said part one, a plurality of sides, said implant having the same number of sides as said bottom end in said opening or passage.

8. The two-part abutment of claim 1 further comprising, at said bottom end of said part one, a plurality of sides, said implant having the same number of sides as said bottom end in said opening or passage.

9. An abutment having a part one and a part two for use with a dental implant having an opening or passage with an internal, non-circular shape at its upper end comprising: part one, having a size and shape, at its bottom end, which is unthreaded and which is adapted to fit sealingly, non-rotatably and unthreadedly into said opening or passage, and, at its top end, means for engaging part two in a plurality of peripherally-spaced positions; part two having means at its bottom end, to sealingly, unthreadedly and non-rotatably engage the top end of said part one, said part two including means for engaging said part one in a plurality of peripherally-spaced positions, said part two including a top end portion adapted to engage or form a prosthesis; said part one and said part two including substantially colinear internal passages for receiving a single threaded fastener to join said part one and said part two to one another, and to the interior opening or passage in said dental implant.

10. The abutment of claim 9 wherein said top end portion lies at an angle with respect to the longitudinal axis of said abutment.

11. The abutment of claim 10 further comprising a single fastener of a size, shape and configuration adapted to join said part one and said part two to one another and to the interior opening or passage in said dental implant.

12. The two-part abutment of claim 11 further comprising, at said bottom end of said part one, a plurality of sides, said implant having the same number of sides as said bottom end in said opening or passage.

13. The two-part abutment of claim 10 further comprising, at said bottom end of said part one, a plurality of sides, said implant having the same number of sides as said bottom end in said opening or passage.

14. The abutment of claim 9 further comprising a single fastener of a size, shape and configuration adapted to join said part one and said part two to one another and to the interior opening or passage in said dental implant.

15. The two-part abutment of claim 14 further comprising, at said bottom end of said part one, a plurality of sides, said implant having the same number of sides as said bottom end in said opening or passage.

16. The two-part abutment of claim 9 further comprising, at said bottom end of said part one, a plurality of sides, said implant having the same number of sides as said bottom end in said opening or passage.

17. An abutment having a part one and a part two for use in a dental implant having an opening or passage with an internal, non-circular shape in its upper end comprising: part one having a size and shape, at its bottom end, which is unthreaded and which is adapted to fit sealingly, non-rotatably and unthreadedly into said opening or passage, and at its top end, a projection having a plurality of sides or faces to engage abutment part two in a plurality of peripherally-spaced positions; part two having means at its bottom end, to sealingly, unthreadedly and non-rotatably engage the top end of said part one, said part two having a cavity of a size and shape complementary to said projection, and adapted to sealingly engage said top end of said part one in a plurality of peripherally-spaced positions, said part two including a top end portion adapted to engage or form a prosthesis; and threaded means for joining said part one and said part two to one another, and to the interior opening or passage in said dental implant.

18. The abutment of claim 17 wherein said top end portion lies at an angle with respect to the longitudinal axis of said abutment.

19. The two-part abutment of claim 18 further comprising, at said bottom end of said part one, a plurality of sides, said implant having the same number of sides as said bottom end in said opening or passage.

20. The abutment of claim 17 further comprising a single fastener of a size, shape and configuration adapted to join said part one and said part two to one another and to the interior opening or passage in said dental implant.

21. The two-part abutment of claim 20 further comprising, at said bottom end of said part one, a plurality of sides, said implant having the same number of sides as said bottom end in said opening or passage.

22. The two-part abutment of claim 17 further comprising, at said bottom end of said part one, a plurality of sides, said implant having the same number of sides as said bottom end in said opening or passage.

* * * * *